United States Patent [19]
Murányi et al.

[11] Patent Number: 4,533,638
[45] Date of Patent: Aug. 6, 1985

[54] BLOOD TYPING APPARATUS

[75] Inventors: István Murányi; Lászlóné Balázs; József Molnár; Ferencné Burda; Mária Metzler; Lajos Szerdahelyi, all of Budapest, Hungary

[73] Assignee: Labor Müszeripari Müvek, Esztergom, Hungary

[21] Appl. No.: 489,660

[22] Filed: Apr. 28, 1983

Related U.S. Application Data

[63] Continuation-in-part of Ser. No. 353,654, Mar. 1, 1982, abandoned, which is a continuation of Ser. No. 208,993, Nov. 17, 1980, abandoned, which is a continuation of Ser. No. 85,218, Oct. 16, 1979, abandoned, which is a continuation-in-part of Ser. No. 941,326, Sep. 11, 1978, abandoned, which is a continuation of Ser. No. 748,053, Dec. 6, 1976, abandoned.

[30] Foreign Application Priority Data

Dec. 30, 1975 [HU] Hungary .................. LA 881

[51] Int. Cl.³ .................................... C12M 1/40
[52] U.S. Cl. .............................. 435/288; 435/284; 435/291
[58] Field of Search .............. 435/284, 288–293, 435/13, 17, 317; 424/11; 422/68, 73, 81–82; 436/53, 520

[56] References Cited

U.S. PATENT DOCUMENTS

| 3,334,018 | 8/1967 | Smythe | 422/73 X |
| 3,605,829 | 9/1971 | Genese et al. | 422/64 X |
| 3,624,223 | 11/1971 | Smythe | 422/73 X |
| 3,690,833 | 9/1972 | Ferrari | 422/82 X |
| 3,700,562 | 10/1972 | Morgenstern et al. | 436/53 X |
| 3,831,618 | 8/1974 | Liston | 422/82 X |
| 3,832,138 | 8/1974 | Hirsch | 422/82 X |
| 3,880,592 | 4/1975 | Kelley et al. | 422/73 X |
| 3,972,778 | 8/1976 | Cunningham | 422/68 X |
| 4,398,894 | 8/1983 | Yamamoto | 422/73 X |

Primary Examiner—R. B. Penland

[57] ABSTRACT

Apparatus for blood-typing comprises a sampler, a reagent recipient, peristaltic pumps serving for the delivery of the reagents and the materials to be examined, a mixer, reactors, a sample-placing device, elements for the control of volume and means for washing.

The mixer is formed as a flattened tube led in a helical line. Before such tube there is a connection for introduction of enzyme.

Means for removal of agglutinate test result are provided. The elements serving for the control of volume are formed by telescopic tubes of variable length.

The device is much simpler than heretofore known devices. It enables achievement of high operational safety and reduction of production and operation cost.

4 Claims, 9 Drawing Figures

BLOOD TYPING APPARATUS

CROSS REFERENCE TO RELATED APPLICATIONS

This application is a continuation-in-part of application Ser. No. 353,654, filed Mar. 1, 1982, now abandoned, which is a continuation of application Ser. No. 208,993, filed Nov. 17, 1980, now abandoned which is a continuation of application Ser. No. 85,218, filed Oct. 16, 1979 and now abandoned, which is a continuation-in-part of application Ser. No. 941,326, filed Sept. 11, 1978 and now abandoned, which in turn is a continuation of application Ser. No. 748,053, filed Dec. 6, 1976 and now abandoned.

The present invention relates to a blood-typing device which is provided with a sampler, is reagent container, peristaltic pumps for delivery of the reagents and the material to be examined, a mixer, reactors, a sample-placer, elements for the control of volume and washing means.

A blood-typing device must meet very rigorous demands. It must operate faultlessly and with high operational safety. Simultaneously, consumption of expensive reagents employed must be kept at a low level.

In order to meet such requirements, development of a suitable apparatus containing elements for performing such basic operations as sampling, washing, mixing, parallel placing of samples from the single channels, control of volume, etc. is of utmost importance since the resultant parameters of the same will determine the qualitative characteristics of the apparatus.

Known blood-typing apparatuses work on the same principal. They operate either in a discrete or in a continuous system.

In the course of the examination, antigen-antibody reactions are probed, resulting in hemoagglutination or absence of same. In order to accelerate the reaction and to increase accuracy of the results, the sample to be examined is mixed with an enzyme. The enzyme does not react with the blood sample but serves instead to accelerate the reaction of antigen with antibodies, if present, in the blood sample. The nature of the reaction and how the test blood serum is employed in the blood typing apparatus is disclosed in Dunsford-Bowley: "Techniques in Blood Grouping", Oliver & Boyd, Edinburgh, 1967.

When using heretofore known devices, a multiple of the quantity of the agent actually needed for achieving a perceptible result must be used because of inaccuracy of sampling, dilution of the sample with wash liquid during the washing operation and insufficient mixing of the sample and the reagent. Consequently, reagent consumption is too high. Methylcellulose has been added to the wash liquid and reagents. Where turbulence occurs in the liquid stream (eg. in distributors, connections, reactors, etc.) deposits of methylcellulose and other kinds of deposits collect and block the liquid stream. This results in an insufficient placing of the sample and intermixture of the samples.

In the aforesaid prior art devices, several channels (generally 8-15) work in parallel. Consequently, parallel readings are required for correct evaluation of the results. If in one or more channels the sample, representing the result of the reaction, is delayed or accelerated, then all samples will not be in the same phase and an incorrect determination will result. The samples can be placed in the same phase by changing the volume of the channel. This can be attained either by cutting out the tube or inserting an extension into the same. This is difficult. Moreover, there is danger of infection when probing the blood of sick people. Flushing of the apparatus is performed by means of a complicated wash-system provided with a multi-channel alternating cock. Clogging occasionally occurs. The straight and arc-like sections of the reactor, which is bent on its shorter sides in the form of a rounded rectangle, provide an alternating resistance to the path of the liquid stream. This results in a pulsating movement of the liquid and in a delayed reaction. Removal of the samples yielding results characteristic for the process is carried out with the aid of a platinum tube protruding into the reactor. In the case of weaker reactions, this makes removal rather uncertain and increases the risk of clogging.

The aim of the present invention is to develop an appropriate system which does not have the heretofore discussed disadvantages of multiple blood-typing devices of the prior art. To stop deposits and intermixture of the samples, a uniform stream of liquid is imperative. It is also required that quick, easy, and appreciable reactions be achieved even in the case of weaker reactions, and that the agglutination quantity needed for evaluation be ensured while simultaneously keeping consumption of samples and reagents at a reasonable level.

Placing the samples coming from the single channels in parallel, i.e. adjusting them into the same phase, must be accomplished without disintegrating the channel. Simultaneously, the complicated multichannel wash-system and the alternating cock should be eliminated.

The present invention is based on the finding that the number of samples needed to achieve highly accurate results can be considerably decreased by eliminating dilution of the sample by the washing liquid and by increasing the intensity of mixing of the sample and reagent. The present invention increases intensity of the washing process, reduces the danger of deposits and reduces consumption of reagents.

Devices, shaped as receivers serving for removal of samples giving the desired result, are arranged within the reactors so that uniform resistance to the stream is obtained. The danger of clogging is thereby reduced. Simultaneously, sensing ability is increased even with weaker reactions.

With the device of the present invention, parallel placing of the samples, representing the results, can be easily performed with the use of elements for the control of volume.

The instant invention relates to a device for blood-typing. The device is provided with a sampler, a reagent container, peristaltic pumps for delivery of the reagents and the material to be examined, a mixer, reactors, a sampler-placer for placing the samples characterizing the results of reactions, elements for the control of volume, and washing means.

The essence of the invention resides in the mixer, which is employed for mixing the enzyme and the blood sample to be examined. The mixer is formed as a flattened tube formed into a helix, before which a connection for the introduction of the enzyme is arranged. The placer, yielding the sample characterizing the result of the examination, contains the elements serving for the control of volume. These elements are expediently in the form of telescoping tubes having changeable length.

The present invention will now be described in detail with reference to a preferred embodiment illustrated in the accompanying drawings in which:

FIG. 2a is a cross section of segment "a" of the mixer of FIG. 2;

FIG. 2b is a cross section of segment "b" of the mixer of FIG. 2;

As used herein, it should be noted that "sample" is intended to cover the blood sample obtained by centrifuging or settling fresh blood to obtain two fractions: cells and plasma.

In blood typing, generally, fifteen factors are examined. Therefore, a corresponding apparatus, would contain fifteen channels, viz. one for each factor examined. Of these fifteen factors, eight are determined by the examination of the cellular fraction of the blood sample and seven are determined from the examination of the plasma fraction of the blood sample. The cellular fraction of the blood sample is introduced into separate channels. The plasma from the blood sample is similarly treated. Each channel has its own series of reactors. The number of channels employed is equal to the number of reagents used, viz. the total number of test plasmas and test cells utilized (eg. for 15 determinations 15 separate channels are required, each with its own reactors (7, 8, 22, 9 and 23).

Figure 1:
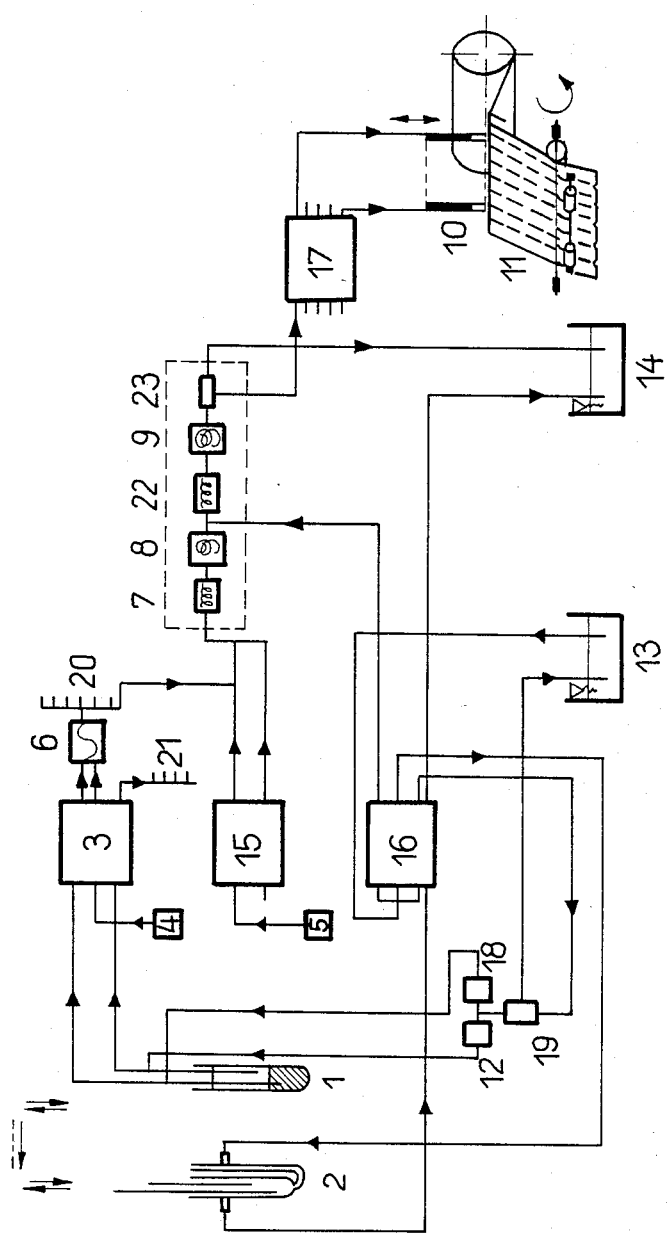
FIG. 1 is a schematical block diagram of a blood-typing device in accordance with the present invention.

As shown in FIG. 1, a double probe (sondes) protrudes into sample storing tube 1. The cell portion of the blood sample is at the bottom of tube 1, while the plasma fraction is above it. The shorter probe evacuates the blood plasma of the test sample while the longer probe evacuates the blood cells of the test sample.

The plasma removed from tube 1 passes through the pump 3 to the distributor 21. The output terminals of the distributor 21, through the pump 15, are connected with a second group of reagent containers or vessels 5 containing test cells through pump 15. The first group of containers 5 contains test blood serum, viz. test plasma, for the blood cell sample coming from the distributor 20. The plasma mixed with different type of test cells (O, A, B, etc.) goes to further "reactors". The total number of containers 5 correspond to the total number of test cells and test plasma used. Further, the number of channels employed in the apparatus is equal to the number of "reactors" present. If, for example, fifteen factors were to be determined, fifteen channels and fifteen reactors would be required.

Further test cells are added from the containers 5 to the plasma of the blood sample which appears on distributor 21 and are also mixed in the mixer 7. The containers 5, containing the test cells and test plasma, are connected to the intake of pump 15. As stated heretofore, there are as many of these containers 5 as there are channels in the apparatus. It is important that the mixture of enzyme and sample cells be always reacted with test plasma and that the plasma of the blood sample be always reacted with test cells. An enzyme pre-sensitized mixture with cells may also be employed.

For purposes of clarity in the drawings only a single container 5 is illustrated. However, as is clear from the above there will be a separate container 5 for each of the test cells and test plasmas. Each of the test cells is fed to a sample of plasma in one of the lines of distributor 21 and each of the test plasmas is fed to a sample of blood cells in one of the lines of distributor 20 in the same manner as illustrated in FIG. 1.

The evacuated cell portion of the sample is delivered to enzyme-mixer 6 by peristaltic pump 3. The enyzme, which serves to accelerate the reaction, is transferred from container or receiver 4 to enzyme-mixer 6 and mixed with the cell portion of the sample.

In brief, in mixer 6, the sample cells are mixed with enzyme. If, as previously stated, the usual fifteen factors are to be determined (eight by examination of the cellular fraction of the blood sample and seven by examination of the plasma part of the sample) then the cellular fraction of the blood sample would be divided, with the aid of divider or distributor 20, into eight branches or channels. To each of these eight channels, a different test plasma would be added from eight different containers 5. The eight channels continue separately and pass through eight separate reactors (each consisting of elements 7, 8, 22, 9 and 23) in which the mixture of cells of the blood sample and enzyme and the test plasma from the containers 5 react with each other and the resultant reaction product agglutinate is removed by result remover 23 and deposited by means of eight different synchronizing elements 10 onto paper 11.

As indicated previously, distributor 20 divides the cellular fraction of the blood sample into eight branches or channels. FIG. 1 illustrates only channels 1 and 8. The other branches, though notshown, operate in the same manner.

Intensive mixing of the cell portion of the sample with the enzyme is of utmost importance. Reactivity of the sample cells with the enzyme and that of the test plasma, as well as the quantity of both the accelerating enzyme and the sample which is needed for analysis, are influenced by the intensity of mixing.

Pump 3 transfers the plasma fraction of the sample from tube 1 into distributor 21 without mixing the plasma fraction with enzyme. The sample plasma is not mixed with enzyme because the enzyme is used only to make the cells of the blood sample more sensitive. The plasma fraction of the blood sample is subdivided by distributor 21 into separate branches (viz. channels). The number of channels used in equal to the number of test cells employed. As stated heretofore, in the generally employed 15 factor determination, seven are determined from examination of the plasma fraction of the blood sample. Consequently, generally, the plasma fraction is divided by distributor 21 into seven separate channels. To each such branch there is added, from seven separate reagent containers 5, a reagent comprising enzymatised test cells. Each of the seven channels communicates with a separate unitary reactor. Each reactor is constituted of elements 7, 8, 22, 9, 23. The results of the reaction in the reactor pass through seven different channels, pump 17, and, by means of elements 10, are deposited onto filter paper 11. The results of the determination (viz. 15 in the usual case) will appear simultaneously and adjacent one another on filter paper 11.

As indicated previously, distributor 21 divides the plasma portion of the blood sample into seven branches or channels. FIG. 1 illustrates channels 1 and 7. The other branches, though not shown, operate in the same manner.

The mixture of the cellular portion of the sample and enzyme delivered from distributor 20 is united with the test serum delivered from the containers 5 by peristaltic pump 15. Thereafter, the mixture is forwarded to the reaction-windings of mixer 7. Mixer 7 serves to mix the mixture of the blood sample cells and enzyme with the test serum. The plasma portion of the sample delivered from distributor 21 is united with the test cells delivered from the containers 5 by peristaltic pump 15. Thereafter, the mixture is forwarded to the reaction-windings of a second mixer which serves to mix the plasma portion of the sample with the test cells.

As stated heretofore, further test cells are added from the containers 5 to the plasma of the blood sample delivered by distributor 21 and are also mixed in the mixer 7. The second group of test cell reagent containers 5 and the first group of test plasma reagent containers 5 are connected to the intake of pump 15. There are as many of these containers 5 as there are channels in the apparatus. It is important that the enzyme and sample cells always be reacted with test plasma and that the blood sample plasma always be reacted with test cells. An enzyme pre-sensitized mixture with cells may also be employed.

Mixer 7, which will be described in greater detail later in this disclosure, is bent in a helix around a horizontal axis. From mixer 7, the sample is transported to winding 8, serving for sedimentation. Winding 8, is shaped as a tube section bent in a helix of larger diameter around a vertical axis. The rotation takes place here. Peristaltic pump 16 transports a physiological saline wash solution to mixer 22. The salt solution is mixed with the mixture of blood sample cells and enzyme and the test plasma. The saline wash serves to prevent false agglutination (sympexis). The next section is the sedimentary section 9, which serves in forming the agglutinate. The presence of agglutinate is indicative of a positive test while absence of agglutinate indicates a negative test result.

Figure 5:
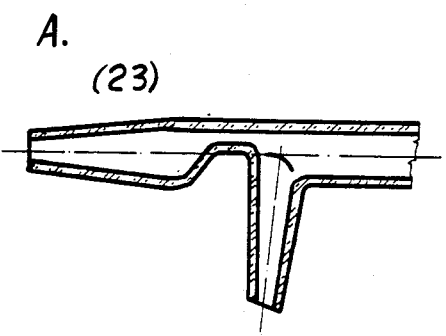
FIG. 5 is an enlarged view of the removing device of FIG. 4.

The agglutinate is removed by peristaltic pump 17 with the aid of removing device (viz. result remover) 23, which operates in a sedimentation-system. "Sedimentation system-like" result remover 23 is novel. In the result remover illustrated in FIG. 5 of the present specification, the liquid arriving from sedimentor 9 enters result remover 23 from the right side. The agglutinate, which forms and represents the result of the test, exits downwardly passing through pump 17 and synchronizing elements 10 before it reaches filter paper 11 upon which it is deposited. Preferably, there is relative movement between the filter paper and the synchronizing elements 10. Most preferably the filter paper, as shown in FIG. 1 is moving. Unnecessary moisture accompanying the deposited agglutinate is removed from the filter paper by means of a suction head (not shown) disposed below the paper and connected to a vacuum pump (not shown).

Detecting can take place on the basis of the results deposited on the filter paper. The liquid (which contains no information from the point of view of the test) flows from the left outlet of the result remover 23 into container 14. The expression "sedimentation system" is employed because in result remover 23 the suspended agglutinates collide with the constricted pipe wall perpendicular to the direction of the flow of the suspended agglutinates. The velocity of the flowing suspended agglutinates drops and they settle downwardly into the conical pipe which serves as the downward outlet for settled agglutinates. Settling is much more intensive than in prior art result removers. In the device of the present invention, this settling is further assisted by the suction effect of pump 17, which is connected to the downward outlet shown in FIG. 5. The sedimenting type result remover of the instant invention is capable of removing agglutinate barely visible to the naked eye.

The cross section of the righthand pipe of result remover 23 is considerably larger than the downward and the lefthand pipes. The two latter pipe cross sections are about identical.

The above mentioned construction of the result remover 23 serves to increase the sensitivity of the apparatus of the present invention and additionally reduces the reagent and sample quantities required for the test.

The removed agglutinate is transported through element 10, which serves for control of volume, and deposited on movable filter paper 11. This is more fully shown in FIG. 3. Excess moisture may be removed from the filter paper 11 by a suction head disposed below the filter paper and connected to a vacuum pump. Element 10 is preferably shaped so that by adjusting the displacement of tube 35 within larger diameter tube 34 the volume of the channel can be increased or decreased respectively. Thus parallel placing of numerous agglutinates (viz. test results) in phase can be performed without the need for dismantling the tube system. As used herein "in phase" means the synchronous, and simultaneous deposition of the agglutinates on filter paper 11. The aim being to make the results of numerous tests (or determinations) appear on the filter paper 11 all at the same time and in a parallel manner, viz. in a straight line.

Figure 3:
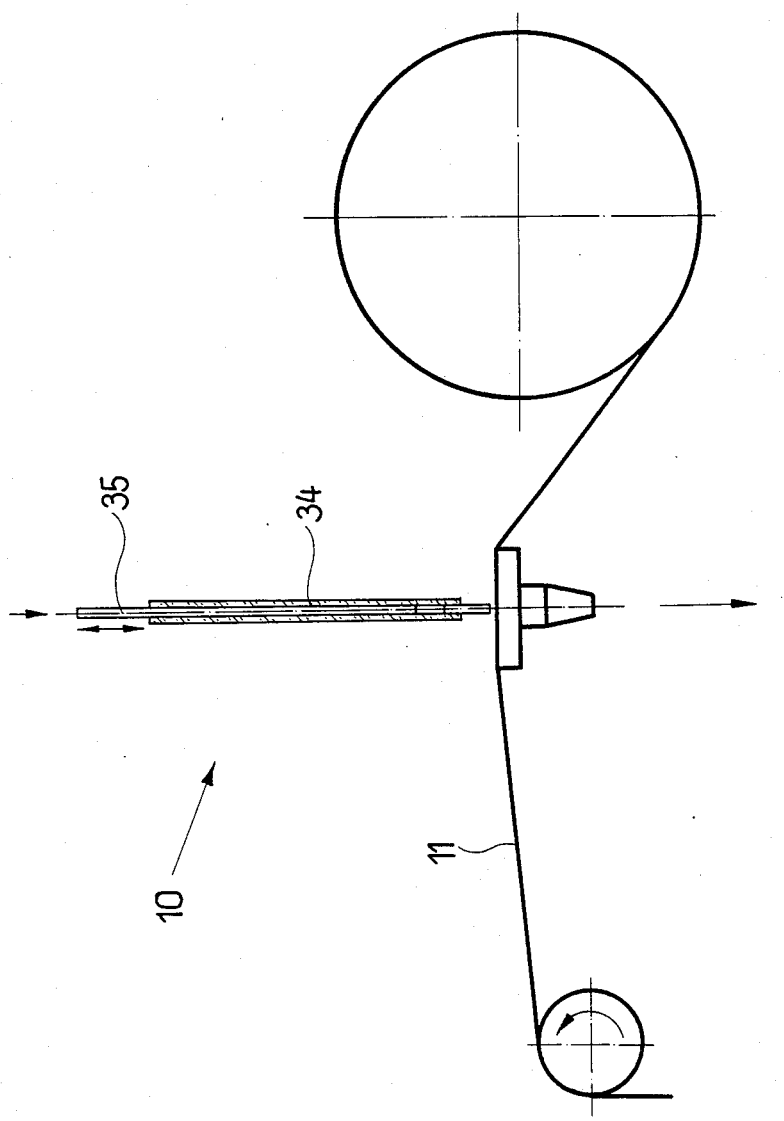
FIG. 3 shows the element for control of volume.

Although, in the present invention, the rate of flow of the samples and reagents is kept constant, the synchronous operation (viz. the simultaneous arrival of results onto the filter paper) depends upon the volumes of the parallel channels and the performance of the pumps. The synchronous operation can be achieved only if the channel volumes are identical at identical pump performance. Because this cannot be easily achieved (due to manufacturing difficulties, viz. varying performance of liquid transfer by the pumps and fabrication inaccuracies of the volume of the channels), the volumes of the channels are adjusted through telescoping arrangement of the synchronizing elements 10. As FIG. 3 shows, the smaller diameter tube 35 can be telescopically moved within the larger tube 34. Inotherwords, tube 35 can be moved in and out of tube 34. Thus, the volumes of the channels can be adjusted so that the results of the tests, which are carried out in a parallel manner, appear simultaneously beside one another (viz. in a single line) on the filter paper 11. This adjustment of the equipment has to be carried out only once. A subsequent adjustment may be needed from time to time, such as for example, for control purposes. Elements 10 are preferably arranged on one common supporting bridge so that simultaneous adjustment of the elements is made possible.

Figure 6:
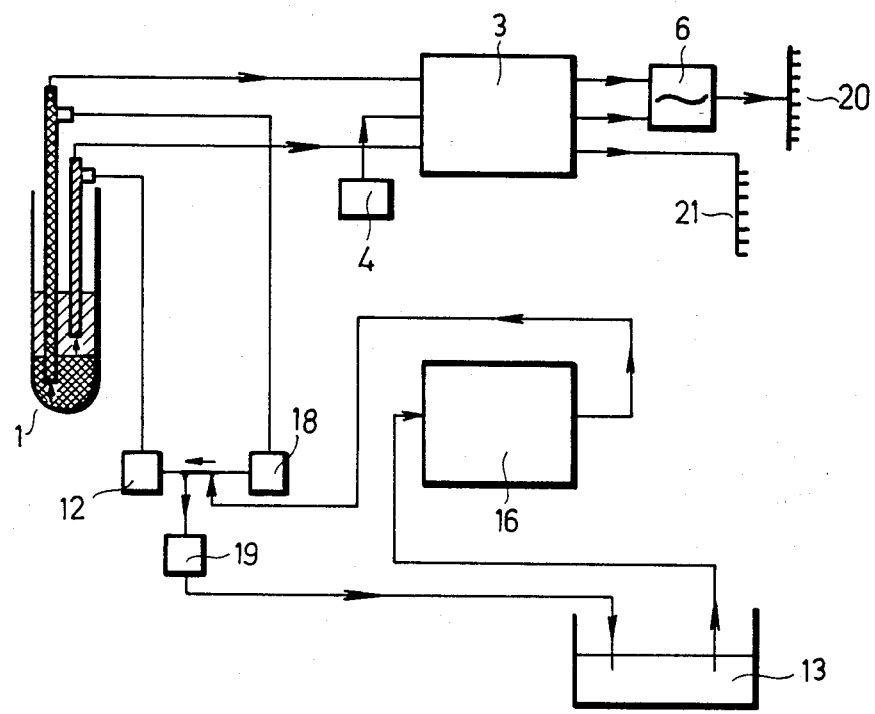
FIG. 6 is a schematical block diagram showing the probes (sondes) immersed in the sample storing tube and illustrating the apparatus for washing during the sampling step.
Figure 7:
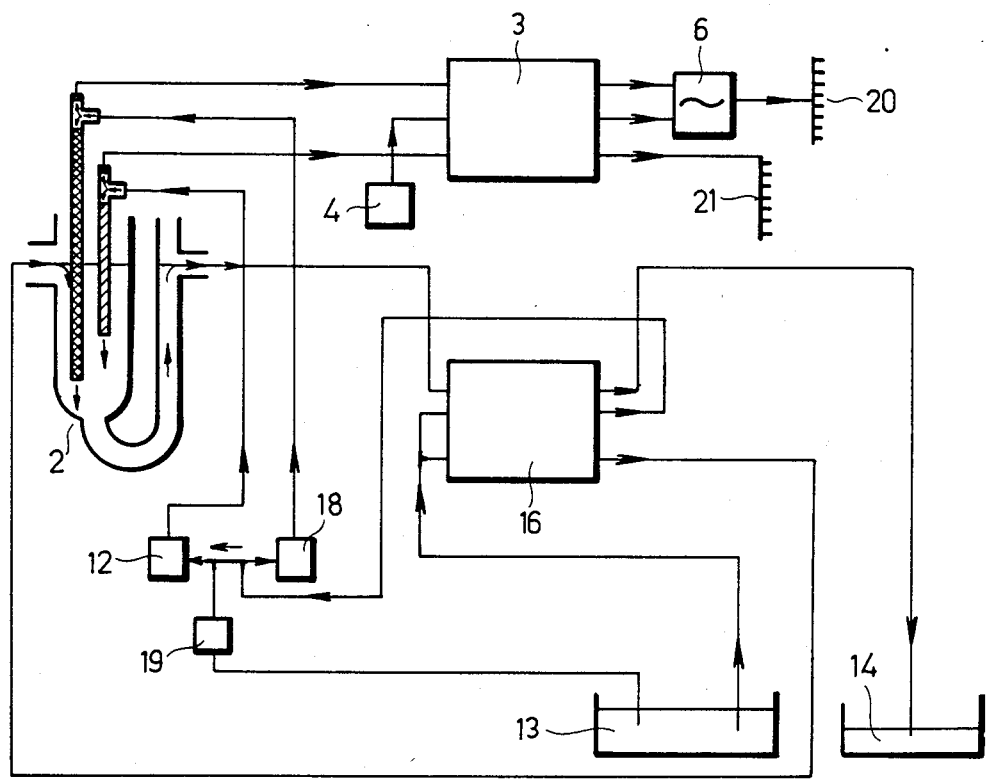
FIG. 7 is a schematical block diagram showing the probes (sondes) in the washer and illustrating the washing step.

The washing operation of the apparatus of the present invention is more fully illustrated in FIGS. 6 and 7. FIG. 6 illustrates the position of the probes (sondes) during the sampling operation. The double probe or sonde is immersed in sample storage tube 1. When it is in such position, electromagnetic valves 12 and 18 are closed while electromagnetic valve 19 is open. Pump 3 draws plasma by suction from the blood sample storing tube 1 through the shorter sonde and the longer sonde draws cells by suction and conveys them towards the reactors for analysis. The washing liquid transport pump 16, which assures circulation of the washing liquid, continually operates. Consequently, it works during the sampling step. Because electromagnetic valves 12 and 18 are closed during the sampling step, the washing liquid cannot flow towards the sondes but only through the electromagnetic valve 19 which is open. Consequently, it returns to the washing liquid container 13. Thus, the washing liquid circulates "without utility" during the sampling step.

Upon completion of the sampling step, an automatic sampler, such as described in U.S. Pat. No. 4,022,067, lifts the sondes out of tube 1, turns them and places them into the washer 2. The washing step, as illustrated in FIG. 7, is then initiated.

When the sondes are lowered into the washing vessel 2, electromagnetic valve 19 closes the path to container 13. Simultaneously, electromagnetic valves 12 and 18 open. The washing liquid, which circulates in washer 2, washes off the surfaces of the sondes. Washing liquid streams through the entry port on the side of the sondes, contacts the sample perpendicularly and cuts it. The lower part of the sample is pressed back by the washing liquid into the washing vessel 2, making it impossible for diluted sample contaminated with the washing liquid to get into the analysis. This step is called countercurrent washing of the sondes. A further advantage of the countercurrent washing is that the fibrous components of the blood (e.g. fibrin) can get stuck when transported in only one direction, but when washed in countercurrent the stuck fibrous components are removed by the washing liquid. Thus, plugging of the sonde is avoided. Another advantage of countercurrent washing is that with non-countercurrent washing the sonde transports, from washing vessel 2, washing liquid contaminated by previous samples. In contrast thereto, with countercurrent washing, the sample is followed by clean washing liquid from the washing liquid container 13 by means of the pump 16 through magnetic valves 12 and 18. This assures perfect washing of the analytical system. Pump 16 pumps clean washing liquid into washing vessel 2 to wash the outer surface of the sonde. Contaminated wash liquid is removed from the opposite side of washing vessel 2 by pump 16 and transported to refuse container 14.

The paths of the liquid streams (sample, washing liquid) are shown in FIGS. 6 and 7 by arrows. The opening and closing of the electromagnetic valves is controlled by the aforementioned automatic sample taker.

In the course of the washing procedure, fast operation of the valves, fast opening and closing in the entire cross-section, as well as absolutely synchronized operation of the single valves are imperative. It is of utmost importance that the valves comply with such requirements even for a longer period. The construction and volume of the probe, as well as the quantity of samples required for analysis, exert an influence on the quality of washing procedure.

Valves 12, 18, and 19 are built so that their pass-through cross sections are identical to the cross sections of the pass-through tubes. Thus, there is no undesireable dead space in the valves. This allows for washing effects that make possible reduction of the amount of sample required for analysis as well as reduction of the amount of reagent needed for the determination. Moreover, the need for multiple channel switching valves (and the alternating cock) is obviated. Consequently, the apparatus of the present invention is considerably simpler than heretofore known devices.

Containers 4 and 5, containing the reagent, are preferably formed as one single module and serve for the performance of all operations utilizing reagents and chemical agents, such as for instance, mixing, temperature control, etc.

Figure 4:
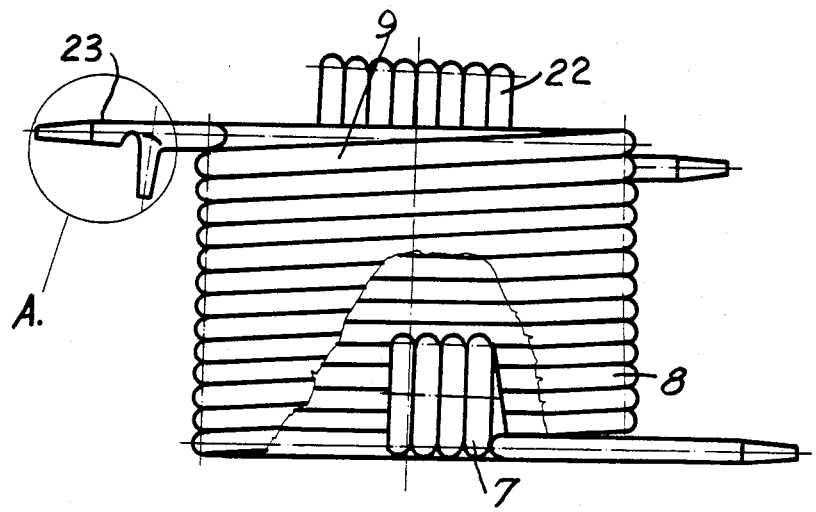
FIG. 4 is a perspective view of one of the circular channels which ensures uniformity of the stream, and also illustrates operation of the removing device in a sedimentary system.

In order to be able to accelerate rapid development of reactions and to reduce the danger of deposits in the reactors (consisting of mixers 7 and 22 and sedimentators 8 and 9) circular windings are formed so as to yield a more uniform resistance with respect to streaming. Result remover 23 is provided for removal of the sample agglutinate test results. Valuable results are ensured even in the case of weaker reactions (FIG. 4).

Figure 2:
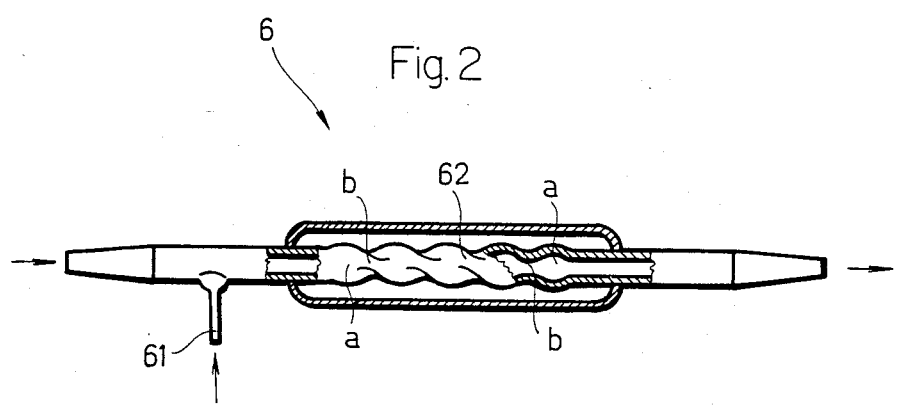
FIG. 2 is an enlarged view of the mixer of the device of FIG. 1.

To achieve more intensive mixing, mixer 6 (as shown in FIG. 2) is used for mixing the enzyme and the sample. As stated heretofore, mixer 6 is formed by a flattened tube 62 shaped into a helix. Before said tube an enzyme-connection 61 is arranged. The essence of enzyme mixer 6 is the flattened tube 62 which is twisted several times around its horizontal axis. As is seen in FIG. 2, the flattened tube 62 is not coil-shaped but is instead twisted about its own longitudinal axis. By twisting the flattened tube, a varying cross section results. The mixing in tube 62 is highly effective because in addition to helical streaming the tube 62 has a nonuniform cross section due to the twisting. Consequently, there is a varying stream velocity along the tube, with a comminution effect resulting. The liquid which flows in the varied cross section tube 62 undergoes pressure and velocity changes according to the variations in the cross section of the tube. Tube 62 thus presents a series-connected confuser-diffuser. The liquid flowing through tube 62 flows through the constrictions and wider portions in a helical path and consequently is in constant turbulence (due to the pressure variations brought about by the flow). Thus the stuck-together cells and the clotted blood particles are separated from one another and the sample mixes well with the enzyme that is introduced through enzyme connector 61. This enables solvation (i.e. the separation and dispersing of the cells in the enzyme) to take place.

Theoretically, the intensity of the mixing, comminution, etc. depends on the magnitude and direction of the forces acting on a unit amount of material. Therefore, it is very important that the forces causing mixing create an effect from all directions (x, y, z planes). Mixer 6 is intended to realize this theoretical consideration.

The mixer 6 comprises a conical portion which communicates with a straight circular cross section pipe. The sample injecting joint 61 communicates with this pipe section and is disposed perpendicularly to the horizontal axis of the pipe section. The straight pipe section communicates with section "a" which in turn communicates with section "b" which is then followed by a second section "a", etc. By connecting sections "a" and "b" in series, a mixer of desired intensity can be created. The pipe section communicates with an exit port of circular cross section which communicates with a terminal conical end portion. The section "a" and "b" can be produced from a flattened cross section pipe corresponding to the section "a". This is accomplished by heating such flattened cross section pipe at a place corresponding to the "b" section and then twisting it around its axis. FIG. 2a shows a cross sectional view of pipe section "a" while FIG. 2b shows a cross sectional view of the segment "b". FIG. 2b represents a view along the line perpendicular to that of the line on which FIG. 2a is shown. The "a" section can be represented as a pair of opposed diffusers and confusers, while the "b" section can be represented as a choke.

As shown in FIG. 2, the pump pushes the materials to be mixed (the enzyme and the cells of the material to be tested) through the mixer in the direction shown by the arrows. In the diffuser portion of the section "a" of the mixer the velocity of flow diminishes (the pressure increases). In the confuser portion, it again accelerates and the change in velocity causes turbulence, which in turn, results in mixing. The confuser terminates in the "b" section. The velocity of the mixture reaches its maximum at this point because the cross section of the mixing space is reduced to a minimum (to 50 microns) and thus the stuck together cells are also mechanically separated. After that the process is repeated in the same manner as described above until the mixture leaves the mixing space.

In summary, the work of the mixer is a composite one. The reduced cross section mechanically separates the stuck together cells. The change in velocity causes turbulence. Moreover, by twisting the flat tube around its axis the direction of flow of the mixture is changed. This results in a very strong mixing action.

The device of the present invention is simpler than prior art devices heretofore known. Moreover, it offers increased operational safety and lower production and operation costs. Further advantageous features include decreased risk of infection and ease of operation.

The compactness of the "reactor", consisting of helical tubes built together, and the construction of the removing device 23 (working on the sedimentation principle) are other advantageous features of the present invention. Moreover, in the present invention, elements 7, 8, 9, and 22 are combined to form a single unit. Such combination has not been heretofore appreciated by the prior art. The liquid that flows through combined elements 7, 8, 9 and 22 flows without turbulence. Additionally, there is no separation of material and no sample contamination. Such separation and contamination would be unavoidable at the connecting points of elements 7, 8, 9, and 22 if they were comprised of individual components.

What is claimed is:

1. In a device for simultaneous multiple blood typing comprising a blood sample container for holding a blood sample containing sample blood cells and sample plasma, a plurality of sample blood cell testing arrangements and a plurality of sample plasma testing arrangements; each member of said plurality of sample blood cell testing arrangements comprising:
    (a) an enzyme storage container;
    (b) an enzyme mixer for mixing sample blood cells with enzyme;
    (c) means for delivering sample blood cells from said blood sample container to said enzyme mixer;
    (d) means for delivering enzyme from said enzyme container to said enzyme mixer;
    (e) a first reactor;
    (f) means for delivering the mixture of enzyme and sample blood cells from said enzyme mixer to said first reactor;
    (g) reagent plasma storage means;
    (h) means for delivering said reagent plasma to said first reactor; and
    (i) means for delivering the reaction product from said first reactor onto a moving web of filter paper; each member of said plurality of sample plasma testing arrangements comprising:
    (j) a second reactor;
    (k) means for delivering sample plasma from said blood sample container to said second reactor;
    (l) a reagent container containing test blood cells;
    (m) means for delivering said test blood cells to said second reactor;
    (n) means for mixing said test blood cells with said sample plasma; and
    (o) means for delivering the reaction product formed by the interaction of said sample plasma and test blood cells onto a moving web of filter paper; the improvement comprising said enzyme mixer having a flatened tubular member twisted about its longitudinal axis so that the tubular member has varying cross section; said first and second reactors each comprising a unitary tubular reactor-sedimentor consisting of a tubular first mixing portion bent in a helix around its horizontal axis and a tubular first sedimentor portion which is unitary with the first mixing portion and bent in a helix around its vertical axis; a tubular saline mixing portion for mixing the enzyme and blood cells of the sample with saline wash solution to prevent false agglutination; the saline mixing portion being unitary with the first sedimentor portion and bent in a helix around its vertical axis, and a tubular second sedimentor portion unitary with the saline mixing portion and bent in a helix about its vertical axis; said device further including means for removing agglutinate from the second sedimentor portion of the tubular reactor-sedimentor which agglutinate indicates of a positive test result; means for maintaining rate of flow in the device substantially contant; volume adjustment means communicating with the means for removing the agglutinate, the volume adjustment means adjusting flow volume so that agglutinate is removed and deposited onto a moving filter paper simultaneously and in a single line from the terminal ends of said plurality of sample blood cell testing arrangements and said plurality of said sample plasma testing arrangements.

2. The device, as claimed in claim 1, wherein the volume adjustment means comprises a first tube having a longitudinal first bore, a second tube having a longitudinal second bore and disposed within the first bore, the second tube and the first tube being longitudinally moveable relative to one another in a telescoping manner.

3. The device, as claimed in claim 1, wherein said means for removing the agglutinate is unitary with and comprises a portion of the tubular reactor-sedimentor.

4. The device, as claimed in claim 1, wherein said means for removing the agglutinate is a substantially T-shaped tubular member having a horizontal inlet tubular portion communicating with the second sedimentor portion, a horizontal outlet tubular portion, and a downwardly extending substantially vertical tubular portion, the horizontal inlet and outlet portions and the downwardly extending substantially vertical portion communicating with one another, the horizontal outlet tubular portion having a constriction, the downwardly extending substantially vertical portion communicating with the horizontal portions between the constriction and the second sedimentor portion, said constriction serving to impede the flow of liquid in said outlet portion whereby agglutinate suspended in the flowing liquid collides with the constriction, loses velocity and is removed from the liquid through the downwardly extending substantially vertical portion.

* * * * *